United States Statutory Invention Registration [19]

[11] Reg. Number: H728

Wallace et al. [43] Published: Feb. 6, 1990

[54] ARYLOXY P-BENZIDINE COMPOUNDS

[75] Inventors: J. Shield Wallace, Albuquerque, N. Mex.; Fred E. Arnold, Centerville, Ohio

[73] Assignee: The United States of America as represented by the Secretary of the Air Force, Washington, D.C.

[21] Appl. No.: 249,621

[22] Filed: Sep. 26, 1988

[51] Int. Cl.[4] ..... C07C 87/50
[52] U.S. Cl. ..... 564/309
[58] Field of Search ..... 564/309, 430

[56] References Cited

U.S. PATENT DOCUMENTS

| | | | |
|---|---|---|---|
| 2,640,081 | 5/1953 | Farkas et al. | 564/309 |
| 3,859,341 | 1/1975 | Jonsson et al. | 260/518 R |
| 4,008,267 | 2/1977 | Jonsson et al. | 260/509 |
| 4,066,408 | 1/1978 | Jonsson et al. | 23/230 R |

OTHER PUBLICATIONS

Wallace et al., "Polym. Prepr.", vol. 28, No. 2, pp. 316–317 (Aug. 1987).

Hunger et al., "Chemical Abstracts", vol. 106, p. 6431, Section No. 64325z (1987).

Sutherlin et al., "Macromolecules", vol. 18, pp. 2669–2675 (1985).

*Primary Examiner*—John F. Terapane
*Assistant Examiner*—Richard Treanor
*Attorney, Agent, or Firm*—Donald J. Singer; Charles E. Bricker

[57] ABSTRACT

There are provided substituted p-benzidines of the formula

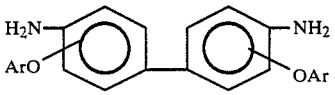

wherein Ar is phenyl or phenoxyphenyl.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ARYLOXY P-BENZIDINE COMPOUNDS

RIGHTS OF THE GOVERNMENT

The invention described herein may be manufactured and used by or for the Government of the United States for all governmental purposes without the payment of any royalty.

BACKGROUND OF THE INVENTION

This invention relates to substituted p-benzidines.

Considerable research effort has been directed toward the synthesis of rigid rod polymers for their unique ordering properties that provide extremely high modulus/high strength films and fibers. One class of materials of particular interest is the aromatic heterocyclic bisbenzazole polymers. These polymers exhibit excellent thermal and thermooxidative stabilities. Another class of materials having comparable high temperature properties is the aromatic polyimides. The polyimides are attractive, not only for their high temperature properties, but also because of the low cost of the diamine and dianhydride monomers used in their synthesis.

An aromatic polymide with the desired para-ordered geometry and be prepared from pyromellitic dianhydride (PMDA) and p-phenylene-diamine. High molecular weight polyamic acid has been prepared in dimethylacetamide (DMAC) using these monomers; however, thermal or chemical cyclodehydration leads to an insoluble, infusible material. Fabrication of this material is normally carried out via the DMAC-soluble polyamic acid which produces two units of water per repeat unit during high temperature thermal cyclodehydration to the imide structure. The water produced by this process limits the utility of this material, particularly in the fabrication of thick components.

It is known that certain polyisoimides can be used to form the corresponding polyimides by thermal curing. Such polyisomides may be prepared by reacting a carboxylic acid dianhydride with a tetravalent aromatic diamine to produce a polyamic acid, and treating the resulting polyamic acid with a dehydrating agent to produce the corresponding polyisoimide. The polyisoimide to polyimide route is attractive from the standpoint that in the course of thermal curing no water vapor is released which could cause voids or defects in thick components. In general, the soluble polyisoimides prepared from aromatic diamines disclosed in the prior art are not linear, i.e., that portion of the polymer backbone contributed by the diamine is either not para-oriented with respect to the amino groups, or contains a non-linear constituent.

As mentioned previously, the aromatic polyimide prepared from pyromellitic dianhydride and p-phenylene diamine has the desired para-ordered geometry. This polymer has attractive high temperature properties and low cost. Unfortunately when prepared via the soluble polymic acid route, the utility of the polymer is limited because of the water produced in the thermal cyclodehydration step.

We attempted to prepare a polyimide from pyromellitic dianhydride and p-phenylene diamine via the polyisoimide to polyimide route. We found that the polyisoimide prepared from these monomers was insoluble in all the solvents tested.

Accordingly, it is an object of the present invention to provide p-benzidine compounds which, when reacted with pyromellitic dianhydride, provide soluble polyisoimides.

Object objects of the invention will be apparent to those skilled in the art.

DESCRIPTION OF THE INVENTION

In accordance with the present invention, there are provided substituted p-benzidines of the formula

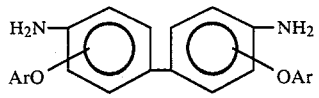

I wherein Ar is phenyl or phenoxyphenyl.

The compounds of this invention are prepared as shown by the following reactions:

A.

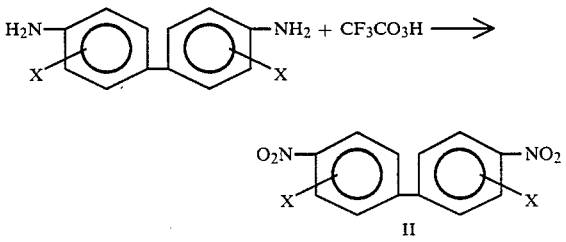

B.

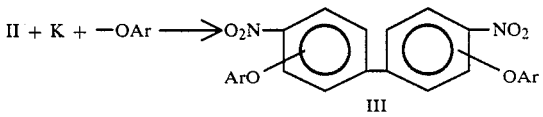

C.

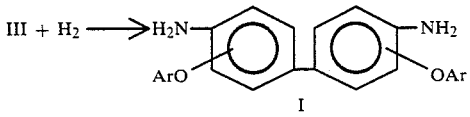

In reaction A, above, wherein X is a halogen such as Cl or Br, a dihalo-p-benzidine is oxidized to provide the corresponding dihalo-4,4′-dinitrobiphenyl. The reaction is carried out in a suitable reaction medium, such as methylene chloride, at a temperature in the range of about 0° C. to 20° C. A presently preferred oxidizing agent is peroxytrifluoroacetic acid.

In the next step of the synthesis as shown by reaction B, each halogen moiety in the dihalo-4,4′-dinitrobiphenyl is replaced by an aryloxy group. The dihalo-4,4′-dinitrobiphenyl prepared above is reacted with the potassium or other alkali metal salt of phenol or a phenoxyphenol, such as 3-phenoxyphenol, to provide the corresponding diaryloxy-4,4′-dinitrobiphenyl. The reaction is carried out at a temperature of about 50° C. to 70° C. for about 1 to 4 hours.

In the final step of the synthesis, as shown by reaction C. the diaryloxy-4,4′-dinitrobiphenyl is hydrogenated, using a suitable hydrogenation apparatus to provide the desired aryloxy-p-benzidine.

The substituted p-benzidines of the present invention are useful in preparing soluble isoimide polymers which can be thermally converted to rod-like, para-ordered imide polymers.

The following examples illustrate the invention:

EXAMPLE I

3,3'-dichloro-4,4'-dinitrobiphenyl

Step 1. Preparation of 3,3'-dichlorobenzidine 150.0 g (0.46 mole) of 3,3'-dichlorobenzidine dihydrochloride was dissolved in 80% ethanol at 50° C., under a nitrogen atmosphere. After the solution was at 50° C., for 30 minutes, it was filtered under a nitrogen atmosphere. To the cooled solution 138 g (1.0 mol) of anhydrous potassium carbonate was added to small portions with stirring. After the addition was completed, stirring was continued for an additional 45 minutes under nitrogen. The solid which formed was collected by vacuum filtration ($N_2$) and washed with water, after which the free amine was dried in a vacuum oven at 40° C. for 48 hours. The weight of the free amine obtained from this procedure was 82 g (70% yield).

Step 2. Preparation of 3,3'-Dichloro-4,4'-Dinitrobiphenyl

To a four-necked, 5 L round-bottom flask, equipped with mechanical stirrer, addition funnel, thermometer reflux condenser, and ice water bath, were added 1500 ml of methylene chloride and 90 ml of 90% hydrogen peroxide. Once the temperature of the solution was at 10° C. 386 ml of perfluoroacetic anhydride addition was completed. 69.0 g (0.273 mol) of 3,3'-dichlorobenzidine was added in small portions (approximately 5 g each) while maintaining the temperature of the reaction mixture at 10° C. After this, the reaction flask was cooled in an ice bath. The yellow solid which formed was collected by vacuum filtration and washed with water. The filtrate was reduced to one fourth its original volume. The additional solid formed was vacuum filtrated, washed with water, and added to the original precipitate collected. The combined solid was air dried for 24 hours and recrystallized twice from acetone/water (2:1) to yield 61.0 g (0.198 mole; 72.5% yield) of 3,3'-dichloro-4,4'-dinitrobiphenyl which melted at 221°-222° C.; IR (KBr) 1520 1325 $cm^{-1}$ ($NO_2$); 1600, 855, 750 $cm^{-1}$ (aromatic);

Anal. Calcd. for $C_6H_6N_2O_4Cl_2$: C, 46.03, H, 1.93; N, 8.95; Cl, 22.65. Found: C, 45.91; H, 1.96; N, 9.01; Cl. 22.73.

EXAMPLE II

3,3'-phenoxy-4,4'-Dinitrobiphenyl

To a 50 ml, three-necked, round bottom flask, equipped with magnetic stir bar and nitrogen inlet/outlet, was added 30 ml of dry DMSO. While stirring under nitrogen, phenol (3.37 g. 36.0 mmol) and potassium methoside (2.14 g, 38.0 mmol) were added. The mixture was stirred at 40° C. for 1 hour after which generation of the potassium salt was judged complete. A 250 ml, three-necked round bottom flask was equipped with gas inlet/outlet, addition funnel, and magnetic stir bar and charged with 3,3'-dichloro 4,4'-dinitrobiphenyl (5.0 g, 11.0 mmol) dissolved in 40 ml of dry DMSO (heating to 60° C., was required to form a clear orange solution). The potassium salt of phenol was transferred (under $N_2$) to the addition funnel and added to the above solution over a period of 1 hour. The solution turned much darker and the reaction temperature was maintained at 60° C., for an additional 2 ½ hours. The reaction mixture was poured into 700 ml of 1N sodium hydroxide and stirred. A precipitate formed (orange) and was collected by suction filtration, washed (on the filter) with 200 ml of distilled water, dissolved in 200 ml of methylene chloride, dried (magnesium sulfate), and filtered, The filtrate was concentrated (rotary evaporator) and crystallized on standing. The crude orange solid was recrystallized from ethyl acetate/hexanes (1/5) to yield 4.82 g (70.5%) of a light orange solid: mp 158°-159° C.; IR (KBr) 1520,1325 $cm^{-1}$ ($NO_2$), 1210 $cm^{-1}$ (ArOAr); $^1H$ NMR 7.95-8.15 (d, aromatic, 1 H), 6.9-7.5 (m, aromatic $^{14}H$): Anal. Calcd. for $C_{24}H_{16}N_2O_{6l:C}$, 67.28, H, 3.77; N, 6.54. Found: C. 67.74; H. 3.89; N. 6.71.

EXAMPLE III

3,3'-(3-Phenoxyphenyleneoxy)-4,4'-Dinitrobiphenyl

To a 50 ml, three-necked, round-bottom flask, equipped with magnetic stir bar and nitrogen inlet/outlet, was added 30 ml of dry DMSO. While stirring (under nitrogen) 3-phenoxyphenol (7.45 g. 40.0 mmol) and potassium methoside (2.95 g. 42.0 mmol) were added. The mixture was stirred at 40° C., for 1 hour, after which generation of the potassium salt was judged complete. A 250 ml, three-necked, round bottom flask was equipped with gas inlet/outlet, addition funnel, magnetic stir bar, and charged with 3,3'-dichloro-4,4'-dinitrobiphenyl (5.0 g, 16.0 mmol) dissolved in 40 ml of dry DMSO (heating to 50° C., was required to form a clear orange solution). The potassium salt of 3-phenoxyphenol was transferred (under $N_2$) to the addition funnel and added to the above solution over a period of 45 minutes. The solution turned much darker and the reaction temperature was maintained at 60° C., for an additional 2 hours. The reaction mixture was poured into 700 ml of 1N sodium hydroxide and stirred. A precipitate formed (orange) and was collected by suction filtration, washed (on a fritted glass funnel) with 200 ml of distilled water, dried (magnesium sulfate), and filtered. The filtrate was concentrated (rotary evaporator) and chromatographed on a quartz column filled with activated silica gel (500 g). The second major band (orange) was eluted with methylene chloride/hexanes (4.1) to yield 6.61 g of a yellow-orange crystalline solid which was recrystallized from ethanol/water (5/1) to yield 5.26 g (54%) of light yellow needles: mp 118.5-119.5° C.; IR (KBr) 1510,1335 $cm^{-1}$ ($NO_2$), 1230 $cm^{-1}$ (ArOAr); $^1H$ NMR 7.92-8.21 (d, aromatic, 2 H), 6.60-7.45 (m, aromatic 22 H): Anal. Calcd. for $C_{36}H_{24}H_2O_8$ C. 70.57; H. 3.95; N. 4.57. Found: C, 70 38; H, 4.05; N, 4.79.

EXAMPLE IV

3,3'-Phenoxy-benzidine

In a 500 ml Paar hydrogenator flask, equipped with mechanical agitator and high pressure hydrogen inlet, were added 3,3'-(3-phenoxy)-4,4'-dinitrobiphenyl (3.40 g, 7.94 mmol), 10% palladium on charcoal (0.3 g), magnesium sulfate (2.5 g), and 100 ml of degassed ethyl acetate. The flask was pressurized to 50 psig and agitated 18 hours. The resulting clear, colorless solution was pressure filtered with nitrogen through diatomaceous filter aid which had been previously washed with dry ethyl acetate to remove the catalyst and magnesium sulfate. The clear filtrate was reduced to half the original volume (rotary evaporator) and 75 ml of hexane added. Upon cooling, large off-white crystals formed and were collected by nitrogen pressure filtration to yield 2.72 g of crude crystalline product. The crude crystals were recrystallized from heptane/methylene chloride (10/1) to yield 2.2 g (75.9%) of light pink plates: mp 126.0°–126.6° C.; IR (KBr) 3595, 3498, 1622 $cm^{-1}$ ($NH_2$), 1210 $cm^{-1}$ (ArOAr); $^1H$ NMR 6.68–7.50 (m, aromatic, 16H), 3.7 (s, amino 4H);

Anal. Calcd. for $C_{24}H_{20}N_2O_2$:C, 78.24; H, 5.47; N, 7.60 Found: C, 78.41; H, 5.64; N, 7.69.

EXAMPLE V

3,3′-(-Phenoxyphenyleneoxy) Benzidine

In a 500 ml Paar hydrogenator flask, equipped with mechanical agitator and high pressure hydrogen inlet, were added 3,3′-bis(3-phenoxyphenyleneoxy)-4,4′-dinitrobiphenyl (5.50 g, 9.0 mol), 10% palladium on charcoal (1.0 g), magnesium sulfate (4.0 g). and 150 ml of degassed ethyl acetate. The flask was pressurized to 50 psig and agitated 20 hours. The resulting clear off-white solution was pressure filtered with nitrogen through diatomaceous filter aid which had been previously washed with dry ethyl acetate to remove the catalyst and magnesium sulfate. The clear filtrate was reduced by half the original volume (rotary evaporator) and 100 ml of hexane added. Upon cooling, small light brown crystals formed and were collected by nitrogen pressure filtration to yield 4.79 g of crude crystalline product which was recrystallized from hexanes/toluene (1/1) to yield 3.88 g (78.02%) of off-white crystalline solid: mp 136°–137° C.; IR (KBr) 3570, 3380, 1628 $cm^{-1}$ ($NH_2$), 1215 $cm^{-1}$ (ArOAr); $^1H$ NMR 6.42–7.51 (m, aromatic, 24 H), 3.69 (s, amino, 4H);

Anal. Calcd. for $C_{36}H_{28}N_2O_4$: C, 78.24; H, 5.11; N, 5.07. Found: C, 78.25; H. 5.33; N, 5.23.

Various modifications may be made without departing from the spirit of the invention or the scope of the appended claims.

We claim:

1. A substituted p-benzidine of the formula

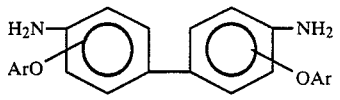

wherein Ar is phenyl or phenoxy phenyl.

2. The compound of claim 1 wherein Ar is phenyl.

3. The compound of claim 1 wherein Ar is phenoxyphenyl.

4. The compound of claim 2 wherein said OAr groups are in the 3 and 3′ positions.

5. The compound of claim 3 wherein said OAr groups are in the 3 and 3′ positions.

6. The compound of claim 5 wherein Ar is 3-phenoxy phenylene.

* * * * *